(12) United States Patent
Roca et al.

(10) Patent No.: US 8,236,490 B2
(45) Date of Patent: Aug. 7, 2012

(54) SCREENING METHOD FOR COMPOUNDS THAT REDUCE ER STRESS

(75) Inventors: Christophe Francois Aime Roca, Lisbon (PT); José Manuel Bernardo Sousa, Lisbon (PT); Marta Isabel Heitor Cerejo, Lisbon (PT); Alexandra Maria Barros Dos Santos, Lisbon (PT); Cátia Santana Reverendo Rodrigues, Lisbon (PT); Ricardo Filipe Antunes Pinheiro, Lisbon (PT); Patricia Ramalhete Mendes da Silva Calado, Lisbon (PT); Sukalyan Chatterjee, Lisbon (PT); Helena Margarida Moreira de Oliveira Vieira, Lisbon (PT)

(73) Assignee: EM Biotecnologia S.A., Lisbon (PT)

( * ) Notice: Subject to any disclaimer, the term of this patent is extended or adjusted under 35 U.S.C. 154(b) by 0 days.

(21) Appl. No.: 12/663,241

(22) PCT Filed: Jun. 6, 2008

(86) PCT No.: PCT/PT2008/000025
§ 371 (c)(1),
(2), (4) Date: May 4, 2010

(87) PCT Pub. No.: WO2008/150186
PCT Pub. Date: Dec. 11, 2008

(65) Prior Publication Data
US 2010/0215641 A1    Aug. 26, 2010

(30) Foreign Application Priority Data

Jun. 7, 2007    (GB) .................................. 0710976.2

(51) Int. Cl.
*C12Q 1/00*    (2006.01)
*C12N 1/00*    (2006.01)
*C12N 15/741*    (2006.01)

(52) U.S. Cl. .................... 435/4; 435/254.11; 435/254.1; 435/483

(58) Field of Classification Search .................. None
See application file for complete search history.

(56) References Cited

U.S. PATENT DOCUMENTS

| 7,439,061 | B2 * | 10/2008 | Kaufman et al. | ............. | 435/325 |
| 2002/0072051 | A1 * | 6/2002 | Bulawa et al. | ................ | 435/4 |

FOREIGN PATENT DOCUMENTS

| WO | 02/00919 | A2 | 1/2002 |
| WO | 03/000853 | A2 | 1/2003 |
| WO | 03/089622 | A2 | 10/2003 |
| WO | 2004/004698 | A2 | 1/2004 |
| WO | 2005/034737 | A2 | 4/2005 |
| WO | 2005/107792 | A2 | 11/2005 |
| WO | 2006/031931 | A2 | 3/2006 |
| WO | 2006/052821 | A2 | 5/2006 |
| WO | 2007/140933 | A1 | 12/2007 |

OTHER PUBLICATIONS

Hou et al. 2007. FEBS J. 274:1637-1650.*
UniProt KB, P02766, http://www.uniprot.org/uniprot/P02766, downloaded Jul. 22, 2011.*
Boorstein et al., "Transcriptional Regulation of SSA3, an HSP70 Gene from *Saccharomyces cerevisiae*," Molecular and Cellular Biology, 1990, pp. 3262-3267, vol. 10, No. 6.
Choo et al., "Deoxyverrucosidin, a Novel GRP78/BiP Down-regulator, Produced by *Penicillium* sp.," J. Antibiot., 2005, pp. 210-213, vol. 58, No. 3.
Gasch et al., "Genomic Expression Programs in the Response of Yeast Cells to Environmental Changes," Molecular Biology of the Cell, 2000, pp. 4241-4257, vol. 11.
Kohno et al., "The Promoter Region of the Yeast KAR2 (BiP) Genen Contains a Regulatory Domain That Responds to the Presence of Unfolded Proteins in the Endoplasmic Reticulum," Molecular and Cellular Biology, 1993, pp. 877-890, vol. 13, No. 2.
Mori et al., "Palindrome with Spacer of One Nucleotide Is Characteristic of the cis-acting Unvolded Protein Response Element in *Saccharomyces cerevisiae*," J. of Biol. Chem., 1998, pp. 9912-9920, vol. 273, No. 16.
Park et al., "Versipelostatin, a novel GRP78/Bip molecular chaperone down-regulator of microbial origin," Tetrahedron Letters, 2002, pp. 6941-6945, vol. 43.
Park et al., "Regulation of GRP 78 Transcription by Substances of Microobial Origin," Society for Neuroscience Abstracts, 2001, p. 1486, vol. 27, No. 1.
Sokka et al., "Endoplasmic Reticulum Stress Inhibition Protects against Excitotoxic Neuronal Injury in the Rat Brain," J. of Neurosci., 2007, pp. 901-908, vol. 27, No. 4.
Umeda et al., "Prunustatin A, a Novel GRP78 Molecular Chaperone Down-Regulator Isolated from *Streptomyces violaceoniger*," J. Antibiot. 2005, pp. 206-209, vol. 58, No. 3.
Yoshida, Hiderou, "ER stress and diseases," FEBS Journal, 2007, pp. 630-658, vol. 274.
Yoshida et al., "Identification of the cis-Acting Endoplasmic Reticulum Stress Response Element Responsible for Transcriptional Induction of Mammalian Glucose-regulated Proteins," J. Biol. Chem., 1998, pp. 33741-33749, vol. 273, No. 50.
International Search Report and Written Opinion, PCT/PT2008/000025, Oct. 30, 2008, European Patent Office.

* cited by examiner

*Primary Examiner* — Shulamith H Shafer
(74) *Attorney, Agent, or Firm* — Joseph R. Baker, Jr.; Gavrilovich Dodd & Lindsey LLP

(57) ABSTRACT

The present invention relates to a cell comprising an Endoplasmic Reticulum (ER) stress element operably linked to a reporter element and an exogenous gene encoding a protein that induces ER stress. Methods of screening using the modified cell, constructs used in the modified cell, the candidate agents identified by the screen and uses thereof are also part of the invention.

9 Claims, 7 Drawing Sheets

SEQ ID 1 (141bp)
CCCGAGGAACTGGACAGCGTGTCGAAAAAGTTGCTTTTTTATATAAAGGA
CACGAAAAGGGTTCTCTGGAAGATATAAATATGGCTATGTAATTCTAAAG
ATTAACGTGTTACTGTTTTACTTTTTTAAAGTCCCCAAGAG

FIG. 1

SEQ ID 2 (444 bp) NM_000371
ATGGCTTCTCATCGTCTGCTCCTCCTCTGCCTTGCTGGACTGGTATTTGTG
TCTGAGGCTGGCCCTACGGGCACCGGTGAATCCAAGTGTCCTCTGATGGT
CAAAGTTCTAGATGCTGTCCGAGGCAGTCCTGCCATCAATGTGGCCGTGC
ATGTGTTCAGAAAGGCTGCTGATGACACCTGGGAGCCATTTGCCTCTGGG
AAAACCAGTGAGTCTGGAGAGCTGCATGGCTCACAACTGAGGAGGAAT
TGTAGAAGGGATATACAAAGTGGAAATAGACACCAAATCTTACTGGAA
GGCACTTGGCATCTCCCCATTCCATGAGCATGCAGAGGTGGTATTCACAG
CCAACGACTCCGGCCCCGCCGCTACACCATTGCCGCCCTGCTGAGCCCC
TACTCCTATTCCACCACGGCTGTCGTCACCAATCCCAAGGAATGA

FIG. 2

SEQ ID 3 (1152 bp) NM_016843
ATGGCTGAGCCCCGCCAGGAGTTCGAAGTGATGGAAGATCACGCTGGGAC
GTACGGGTTGGGGGACAGGAAAGATCAGGGGGGCTACACCATGCACCAA
GACCAAGAGGGTGACACGGACGCTGGCCTGAAAGCTGAAGAAGCAGGCA
TTGGAGACACCCCCAGCCTGGAAGACGAAGCTGCTGGTCACGTGACCCAA
GCTCGCATGGTCAGTAAAAGCAAAGACGGGACTGGAAGCGATGACAAAA
AAGCCAAGGGGGCTGATGGTAAAACGAAGATCGCCACACCGCGGGGAGC
AGCCCCTCCAGGCCAGAAGGGCCAGGCCAACGCCACCAGGATTCCAGCA
AAAACCCCGCCCGCTCCAAAGACACCACCCAGCTCTGGTGAACCTCCAAA
ATCAGGGGATCGCAGCGGCTACAGCAGCCCCGGCTCCCAGGCACTCCCG
GCAGCCGCTCCCGCACCCCGTCCCTTCCAACCCCACCCACCCGGGAGCCC
AAGAAGGTGGCAGTGGTCCGTACTCCACCCAAGTCGCCGTCTTCCGCCAA
GAGCCGCCTGCAGACAGCCCCCGTGCCCATGCCAGACCTGAAGAATGTCA
AGTCCAAGATCGGCTCCACTGAGAACCTGAAGCACCAGCCGGGAGGCGG
GAAGGTGCAGATAATTAATAAGAAGCTGGATCTTAGCAACGTCCAGTCCA
AGTGTGGCTCAAAGGATAATATCAAACACGTCCCGGGAGGCGGCAGTGTG
CAAATAGTCTACAAACCAGTTGACCTGAGCAAGGTGACCTCCAAGTGTGG
CTCATTAGGCAACATCCATCATAAACCAGGAGGTGGCCAGGTGGAAGTAA
AATCTGAGAAGCTTGACTTCAAGGACAGAGTCCAGTCGAAGATTGGGTCC
CTGGACAATATCACCCACGTCCCTGGCGGAGGAAATAAAAAGATTGAAAC
CCACAAGCTGACCTTCCGCGAGAACGCCAAAGCCAAGACAGACCACGGG
GCGGAGATCGTGTACAAGTCGCCAGTGGTGTCTGGGGACACGTCTCCACG
GCATCTCAGCAATGTCTCCTCCACCGGCAGCATCGACATGGTAGACTCGC
CCCAGCTCGCCACGCTAGCTGACGAGGTGTCTGCCTCCCTGGCCAAGCAG
GGTTTGTGA

FIG. 3

SEQ ID 4 (4443 bp) NM_000492
ATGCAGAGGTCGCCTCTGGAAAAGGCCAGCGTTGTCTCCAAACTTTTTTT
CAGCTGGACCAGACCAATTTTGAGGAAAGGATACAGACAGCGCCTGGAA
TTGTCAGACATATACCAAATCCCTTCTGTTGATTCTGCTGACAATCTATCT
GAAAAATTGGAAAGAGAATGGGATAGAGAGCTGGCTTCAAAGAAAAATC
CTAAACTCATTAATGCCCTTCGGCGATGTTTTTTCTGGAGATTTATGTTCT
ATGGAATCTTTTTATATTTAGGGGAAGTCACCAAAGCAGTACAGCCTCTC
TTACTGGGAAGAATCATAGCTTCCTATGACCCGGATAACAAGGAGGAAC
GCTCTATCGCGATTTATCTAGGCATAGGCTTATGCCTTCTCTTTATTGTGA
GGACACTGCTCCTACACCCAGCCATTTTGGCCTTCATCACATTGGAATG
CAGATGAGAATAGCTATGTTTAGTTTGATTTATAAGAAGACTTTAAAGCT
GTCAAGCCGTGTTCTAGATAAAATAAGTATTGGACAACTTGTTAGTCTCC
TTTCCAACAACCTGAACAAATTTGATGAAGGACTTGCATTGGCACATTTC
GTGTGGATCGCTCCTTTGCAAGTGGCACTCCTCATGGGGCTAATCTGGGA
GTTGTTACAGGCGTCTGCCTTCTGTGGACTTGGTTTCCTGATAGTCCTTGC
CCTTTTTCAGGCTGGGCTAGGGAGAATGATGATGAAGTACAGAGATCAG
AGAGCTGGGAAGATCAGTGAAAGACTTGTGATTACCTCAGAAATGATTG
AAAATATCCAATCTGTTAAGGCATACTGCTGGGAAGAAGCAATGGAAAA
AATGATTGAAAACTTAAGACAAACAGAACTGAAACTGACTCGGAAGGCA
GCCTATGTGAGATACTTCAATAGCTCAGCCTTCTTCTTCTCAGGGTTCTTT
GTGGTGTTTTTATCTGTGCTTCCCTATGCACTAATCAAAGGAATCATCCTC
CGGAAAATATTCACCACCATCTCATTCTGCATTGTTCTGCGCATGGCGGT
CACTCGGCAATTTCCCTGGGCTGTACAAACATGGTATGACTCTCTTGGAG
CAATAAACAAAATACAGGATTTCTTACAAAAGCAAGAATATAAGACATT
GGAATATAACTTAACGACTACAGAAGTAGTGATGGAGAATGTAACAGCC
TTCTGGGAGGAGGGATTTGGGGAATTATTTGAGAAAGCAAAACAAAACA
ATAACAATAGAAAAACTTCTAATGGTGATGACAGCCTCTTCTTCAGTAAT
TTCTCACTTCTTGGTACTCCTGTCCTGAAAGATATTAATTTCAAGATAGAA
AGAGGACAGTTGTTGGCGGTTGCTGGATCCACTGGAGCAGGCAAGACTT
CACTTCTAATGGTGATTATGGGAGAACTGGAGCCTTCAGAGGGTAAAATT
AAGCACAGTGGAAGAATTTCATTCTGTTCTCAGTTTTCCTGGATTATGCCT
GGCACCATTAAAGAAAATATCATCTTTGGTGTTTCCTATGATGAATATAG
ATACAGAAGCGTCATCAAAGCATGCCAACTAGAAGAGGACATCTCCAAG
TTTGCAGAGAAAGACAATATAGTTCTTGGAGAAGGTGGAATCACACTGA
GTGGAGGTCAACGAGCAAGAATTTCTTTAGCAAGAGCAGTATACAAAGA
TGCTGATTTGTATTTATTAGACTCTCCTTTTGGATACCTAGATGTTTTAAC
AGAAAAAGAAATATTTGAAAGCTGTGTCTGTAAACTGATGGCTAACAAA
ACTAGGATTTTGGTCACTTCTAAAATGGAACATTTAAAGAAAGCTGACAA
AATATTAATTTTGCATGAAGGTAGCAGCTATTTTTATGGGACATTTTCAG
AACTCCAAAATCTACAGCCAGACTTTAGCTCAAAACTCATGGGATGTGAT
TCTTTCGACCAATTTAGTGCAGAAAGAAGAAATTCAATCCTAACTGAGAC
CTTACACCGTTTCTCATTAGAAGGAGATGCTCCTGTCTCCTGGACAGAAA
CAAAAAAACAATCTTTTAAACAGACTGGAGAGTTTGGGGAAAAAGGAA
GAATTCTATTCTCAATCCAATCAACTCTATACGAAAATTTTCCATTGTGCA
AAAGACTCCCTTACAAATGAATGGCATCGAAGAGGATTCTGATGAGCCTT
TAGAGAGAAGGCTGTCCTTAGTACCAGATTCTGAGCAGGGAGAGGCGAT
ACTGCCTCGCATCAGCGTGATCAGCACTGGCCCCACGCTTCAGGCACGAA
GGAGGCAGTCTGTCCTGAACCTGATGACACACTCAGTTAACCAAGGTCAG
AACATTCACCGAAAGACAACAGCATCCACACGAAAAGTGTCACTGGCCC

FIGURE 4

```
CTCAGGCAAACTTGACTGAACTGGATATATATTCAAGAAGGTTATCTCAA
GAAACTGGCTTGGAAATAAGTGAAGAAATTAACGAAGAAGACTTAAAGG
AGTGCTTTTTTGATGATATGGAGAGCATACCAGCAGTGACTACATGGAAC
ACATACCTTCGATATATTACTGTCCACAAGAGCTTAATTTTTGTGCTAATT
TGGTGCTTAGTAATTTTTCTGGCAGAGGTGGCTGCTTCTTTGGTTGTGCTG
TGGCTCCTTGGAAACACTCCTCTTCAAGACAAAGGGAATAGTACTCATAG
TAGAAATAACAGCTATGCAGTGATTATCACCAGCACCAGTTCGTATTATG
TGTTTTACATTTACGTGGGAGTAGCCGACACTTTGCTTGCTATGGGATTCT
TCAGAGGTCTACCACTGGTGCATACTCTAATCACAGTGTCGAAAATTTTA
CACCACAAAATGTTACATTCTGTTCTTCAAGCACCTATGTCAACCCTCAA
CACGTTGAAAGCAGGTGGGATTCTTAATAGATTCTCCAAAGATATAGCAA
TTTTGGATGACCTTCTGCCTCTTACCATATTTGACTTCATCCAGTTGTTATT
AATTGTGATTGGAGCTATAGCAGTTGTCGCAGTTTTACAACCCTACATCTT
TGTTGCAACAGTGCCAGTGATAGTGGCTTTTATTATGTTGAGAGCATATTT
CCTCCAAACCTCACAGCAACTCAAACAACTGGAATCTGAAGGCAGGAGT
CCAATTTTCACTCATCTTGTTACAAGCTTAAAAGGACTATGGACACTTCGT
GCCTTCGGACGGCAGCCTTACTTTGAAACTCTGTTCCACAAAGCTCTGAA
TTTACATACTGCCAACTGGTTCTTGTACCTGTCAACACTGCGCTGGTTCCA
AATGAGAATAGAAATGATTTTTGTCATCTTCTTCATTGCTGTTACCTTCAT
TTCCATTTTAACAACAGGAGAAGGAGAAGGAAGAGTTGGTATTATCCTG
ACTTTAGCCATGAATATCATGAGTACATTGCAGTGGGCTGTAAACTCCAG
CATAGATGTGGATAGCTTGATGCGATCTGTGAGCCGAGTCTTTAAGTTCA
TTGACATGCCAACAGAAGGTAAACCTACCAAGTCAACCAAACCATACAA
GAATGGCCAACTCTCGAAAGTTATGATTATTGAGAATTCACACGTGAAGA
AAGATGACATCTGGCCCTCAGGGGGCCAAATGACTGTCAAAGATCTCAC
AGCAAAATACACAGAAGGTGGAAATGCCATATTAGAGAACATTTCCTTCT
CAATAAGTCCTGGCCAGAGGGTGGGCCTCTTGGGAAGAACTGGATCAGG
GAAGAGTACTTTGTTATCAGCTTTTTTGAGACTACTGAACACTGAAGGAG
AAATCCAGATCGATGGTGTGTCTTGGGATTCAATAACTTTGCAACAGTGG
AGGAAAGCCTTTGGAGTGATACCACAGAAAGTATTTATTTTTCTGGAAC
ATTTAGAAAAAACTTGGATCCCTATGAACAGTGGAGTGATCAAGAAATA
TGGAAAGTTGCAGATGAGGTTGGGCTCAGATCTGTGATAGAACAGTTTCC
TGGGAAGCTTGACTTTGTCCTTGTGGATGGGGCTGTGTCCTAAGCCATG
GCCACAAGCAGTTGATGTGCTTGGCTAGATCTGTTCTCAGTAAGGCGAAG
ATCTTGCTGCTTGATGAACCCAGTGCTCATTTGGATCCAGTAACATACCA
AATAATTAGAAGAACTCTAAAACAAGCATTTGCTGATTGCACAGTAATTC
TCTGTGAACACAGGATAGAAGCAATGCTGGAATGCCAACAATTTTTGGTC
ATAGAAGAGAACAAAGTGCGGCAGTACGATTCCATCCAGAAACTGCTGA
ACGAGAGGAGCCTCTTCCGGCAAGCCATCAGCCCCTCCGACAGGGTGAA
GCTCTTTCCCCACCGGAACTCAAGCAAGTGCAAGTCTAAGCCCCAGATTG
CTGCTCTGAAAGAGGAGACAGAAGAAGAGGTGCAAGATACAAGGCTTTA
G
```

FIGURE 4 (cont.)

SCREENING METHOD FOR COMPOUNDS THAT REDUCE ER STRESS

CROSS REFERENCE TO RELATED APPLICATIONS

This application is a National Stage Application filed under 35 U.S.C. §371 and claims priority to International Application No. PCT/PT2008/000025, filed Jun. 6, 2008, and published in English on Dec. 11, 2008 as publication no. WO 2008/150186, which application claims priority to Great Britain Application No. 0710976.2, filed on Jun. 7, 2007, the disclosures of which are incorporated herein by reference.

FIELD OF THE INVENTION

The present invention relates to a cell comprising an Endoplasmic Reticulum (ER) stress element operably linked to a reporter element and an exogenous gene encoding a protein that induces ER stress. Methods of screening using the modified cell, constructs used in the modified cell, the candidate agents identified by the screen and uses thereof are also part of the invention.

BACKGROUND

The biological function of cells, and ultimately of tissues, organs and body, depends on the correct folding of a network of thousands of proteins. The amino acid sequence of a given protein contains the required information to fold it into a functional, specific three-dimensional structure. In healthy cells, proteins fold properly into their native conformation and, if they do not, the misfolding should be corrected by chaperone proteins (Bukau B, Weissman J, Horwich A. Cell. 2006; 125(3):443-51). In protein misfolding disorders (PMDs) or conformational disorders (CDs), however, misfolding of a protein results in its degradation (e.g. cystic fibrosis) or in its aggregation and accumulation as protein deposits near the site of its cellular production or in diverse tissues (Soto C, Estrada L D. Arch Neurol. 2008; 65(2):184-9; Winklhofer K F, Tatzelt J, Haass C. EMBO J. 2008; 27(2): 336-49; Gregersen N. J Inherit Metab Dis. 2006; 29(2-3): 456-70).

BRIEF DESCRIPTION OF THE DRAWINGS

The present invention is described with references to the drawings, in which:

FIG. 1 illustrates a 141 bp fragment of the yeast KAR2 promoter (SEQ ID NO:1).

FIG. 2 illustrates a 444 bp fragment containing the coding region of the human TTR gene (SEQ ID NO:2).

FIG. 3 illustrates the coding region of the human Tau protein (isoform 3) (SEQ ID NO:3).

FIG. 4 illustrates the coding region of the wild type human CFTR gene (SEQ ID NO:4).

Figure 5:
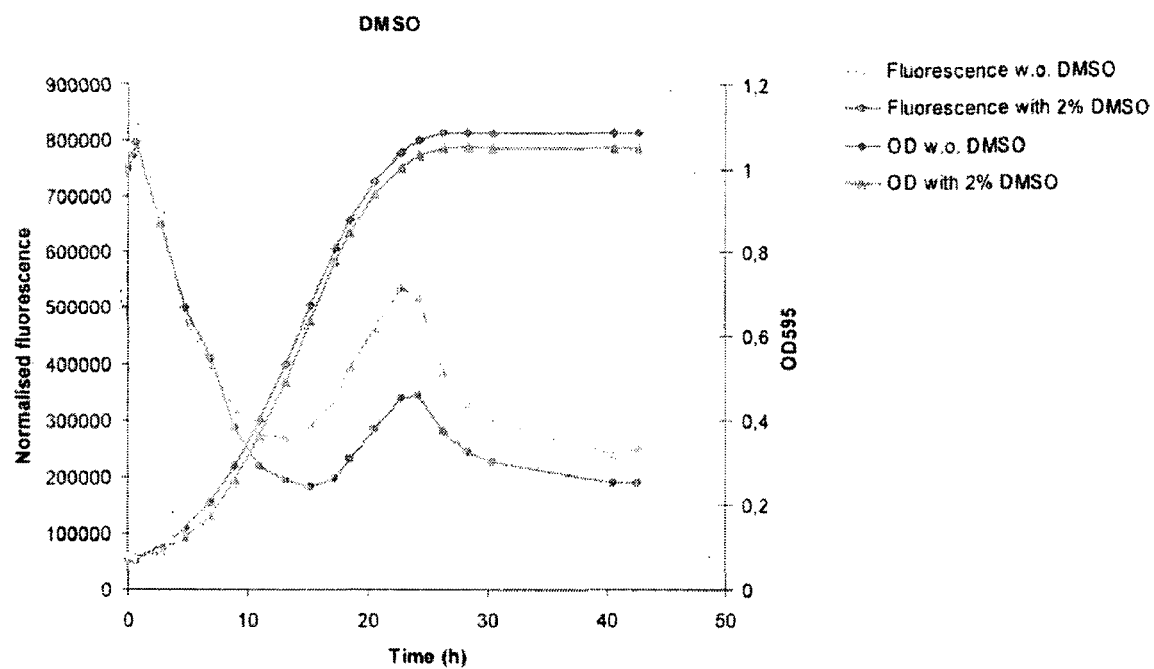
FIG. 5 illustrates growth and fluorescence signal of DGI-TAUP301L cells on minimum medium with 2% galactose, with and without 2% DMSO.

In the figures, where used, the expression "w.o" indicates "without".

DETAILED DESCRIPTION

There are certain mechanisms that are common to the vast majority of protein conformational diseases including aggregate formation, altered transcriptional regulation, mitochondrial dysfunction, induction of ER stress and impairment of the ubiquitin-proteasome system. Induction of ER stress is one of the most common mechanisms associated with protein conformational diseases (Yoshida H. FEBS J. 2007; 274(3): 630-58).

The ER is a major protein-folding compartment in a eukaryotic cell and is second only to the cytosol. Protein folding in the ER is more complex than protein folding in the cytosol because proteins are posttranslationally modified. Folding in the ER must couple protein-synthesis pathways operating outside of the compartment with ER-assisted folding (ERAF) pathways in the lumen. Expression of a mutant version of a protein, or even some-wild-type proteins, viral infection, energy or nutrient depletion, extreme environmental conditions, or stimuli that elicit excessive calcium release from the ER lumen compromise protein-folding reactions in the ER, causing unfolded protein to accumulate and initiate a cascade of signals that are transmitted to the cytoplasm and nucleus. When the protein-folding demand on the ER exceeds the folding capacity of the ER, a condition termed "ER stress" results (Malhotra J D, Kaufman R J Semin Cell Dev Biol. 2007; 18(6):716-31). ER stress can also result from other conditions, namely when a protein that is translated in the cytosol is misfolded and induces the recruitment of the folding machinery, leading to a deficit of folding assistance in the ER.

Chaperone-mediated folding imbalances that are associated with numerous misfolding diseases, (including diabetes, Huntington's disease, Alzheimer's disease, Parkinson's disease, prion encephalopathies, cystic fibrosis and many others), trigger the unfolded-protein response (UPR), using both transcriptional and translational pathways to correct the problem and alleviate ER stress. This adaptative response includes: 1) the transcriptional activation of genes encoding ER-resident chaperones and folding catalysts; 2) protein degrading complexes that augment ER folding capacity and 3) translational attenuation to limit further accumulation of unfolded proteins in the ER. Small-molecule modulators of folding-response pathways provide new pharmacological tools to adjust these imbalances. Reprogramming stress pathways with drugs provides a potential new approach for balancing ER-protein load with cellular-folding capacity, thus correcting the underlying disease.

Some screening methods for identifying ER stress modulators exist, such as that described in WO2005/034737, which describes a mammalian screen involving the use of Inositol Requiring 1 (IRE1) and/or X-box-binding protein-1 (XBP-1) as specific markers of ER stress. However, these screens do not represent a cheap, rapid throughput and sensitive system for identifying ER stress modulators.

As there is an urgent need for therapeutic agents with the potential to prevent and/or treat ER stress-related diseases and disorders, there is a high demand for a rapid, throughput screening method that retains sensitivity.

The present invention provides such a sensitive, rapid and low-cost cell screening platform for compounds that will be useful in the treatment of diseases or disorders related to ER stress.

The first aspect of the invention provides a cell comprising an ER stress sensor element operably linked to a reporter element and comprising an exogenous gene encoding a protein that induces ER stress.

In one embodiment, the cell is a eukaryotic cell. In a further embodiment, the cell is a yeast cell. In yet a further embodiment, a *Saccharomyces cerevisiae* cell or any other Saccharomycetales yeast strain is employed.

The ER stress sensor element can be any component of the signalling pathway known to be activated in response to ER stress conditions, i.e. any component of the unfolded protein response (UPR). An ER stress sensor element is the same as an ER stress marker. Components of the UPR pathway are well known by those skilled in the art and include all the generally designated ER stress markers. An ER stress sensor element of the invention can be a yeast ER stress marker.

One way in which ER stress induces the UPR is by transcriptional activation of target genes. Another way that the UPR is induced is by changes in phosphorylation states, splicing patterns or protein translation of specific genes and proteins. For example, ER stress induces the activation of IRE1 by phosphorylation. Therefore, IRE1 phosphorylation is a marker of ER stress. In another example, Hac1/XBP1 mRNAs are selectively spliced upon ER stress and, therefore, the splicing pattern of Hac1/XBP1 is a marker of ER stress. In a further example, a marker for ER stress is ATF4 translation, as translation of ATF4 is dependent on the activation of the UPR.

Transcriptional activation induced by the UPR can be used as an ER stress marker. In one embodiment, the ER stress sensor element is a DNA sequence corresponding to an unfolded protein response element (UPRE). When in use as an ER stress sensor or marker the DNA sequence is transcriptionally activated. In a further embodiment, the ER stress sensor element is a DNA sequence corresponding to the UPRE of the Hac1, LHS1, PDI1 or KAR2 genes.

The KAR2 UPRE of the invention may comprise i) the nucleic acid sequence as set forth in SEQ ID NO:1, a nucleic sequence that is more than 95% homologous thereto or to its DNA complement or counterpart RNA sequence, a variant, fragment or the complementary strand thereof or ii) a nucleic acid sequence, especially DNA or RNA, which hybridises to the DNA sequence of SEQ ID NO:1, a nucleic acid sequence that is more than 95% homologous thereto or a variant or fragment thereof.

This aspect of the invention extends to a KAR2 UPRE comprising a nucleic acid sequence that is at least 96%, 97%, 98% or 99% homologous with the DNA sequence of SEQ ID NO:1 or with its DNA complement or a counterpart RNA sequence.

Hybridisation may occur under conditions of high stringency. As herein defined, conditions of "high stringency", may be identified by those that: (1) employ low ionic strength and high temperature for washing, for example 0.015 M sodium chloride/0.0015 M sodium citrate/0.1% sodium dodecyl sulphate at 50[deg.] C.; (2) employ during hybridization a denaturing agent, such as formamide, for example, 50% (v/v) formamide with 0.1% (w/v bovine serum albumin/0.1% (w/v) Ficoll/0.1% (w/v) polyvinylpyrrolidone/50 mM sodium phosphate buffer at pH 6.5 with 750 mM sodium chloride, 75 mM sodium citrate at 42[deg.] C.; or (3) employ 50% (v/v) formamide, 5×SSC (0.75 M NaCl, 0.075 M sodium citrate), 50 mM sodium phosphate (pH 6.8), 0.1% sodium pyrophosphate, 5×Denhardt's solution, sonicated salmon sperm DNA (50 [mu]g/ml), 0.1% (w/v) SDS, and 10% (w/v) dextran sulphate at 42[deg.] C., with washes at 42[deg.] C. in 0.2×SSC (sodium chloride/sodium citrate) and 50% formamide at 55[deg.] C., followed by a high-stringency wash consisting of 0.1×SSC containing EDTA at 55[deg.] C.

The percent identity of nucleic acid sequences may be determined as by comparing sequence information using the GAP computer program, version 6.0 described by Devereux et al. (Nucl. Acids Res. 12:387, 1984) and available from the University of Wisconsin Genetics Computer Group (UWGCG). The GAP program utilizes the alignment method of Needleman and Wunsch (J. Mol. Biol. 48:443, 1970), as revised by Smith and Waterman (Adv. Appl. Math 2:482, 1981). The preferred default parameters for the GAP program include: (1) a unary comparison matrix (containing a value of 1 for identities and 0 for non-identities) for nucleotides, and the weighted comparison matrix of Gribskov and Burgess, Nucl. Acids Res. 14:6745, 1986, as described by Schwartz and Dayhoff, eds., Atlas of Protein Sequence and Structure, National Biomedical Research Foundation, pp. 353-358, 1979; (2) a penalty of 3.0 for each gap and an additional 0.10 penalty for each symbol in each gap; and (3) no penalty for end gaps. Other programs used by one skilled in the art of sequence comparison may also be used.

Isolation of the ER stress sensor element nucleotide sequence can be performed by any suitable conventional method known by those of skill in the art, such as PCR amplification or commercial DNA synthesis and hybridization. Appropriate ER stress sensor elements and reporter elements are known to a skilled person.

In yeast, the accumulation of unfolded proteins in the ER activates the production of the Hac1 transcription factor, responsible for activating UPR target genes. A comprehensive study defined the transcriptional scope of Hac1-mediated UPR in yeast to comprise some 400 genes (~5% of the yeast genome) (Travers K J, Patil C K, Wodicka L, Lockhart D J, Weissman J S, Walter P. Cell. 2000; 101(3):249-58). The best-understood upstream activation sequence to which Hac1 binds, the unfolded protein response element 1 (UPRE-1) was identified in the promoter of the UPR target Kar2. However, less than 5% of the yeast UPR target genes contain this sequence element within its promoters, two additional UPREs (UPRE-2 and UPRE-3) also bind Hac-1, although sharing no recognizable sequence similarity. The Hac-1 promoter itself contains an UPRE sequence and responds to ER stress to induce transcription of its downstream gene.

The reporter element comprises a nucleotide sequence coding for a polypeptide efficiently detectable by established methods, preferably providing a readout that is compatible with a high throughput screening assay. The reporter element is expressed when the ER stress sensor element to which it is operably linked is activated. Examples of reporter elements include, but are not limited to, β-galactosidase, alkaline phosphatase, luciferase and tagged proteins. The reporter element can encode, for example, any fluorescent based marker e.g. the yeast enhanced green fluorescent protein, as well as enzymes, immunological markers or any other example of selectable and screenable markers well known in the art. The reporter element is operably linked to the ER stress sensor element and is therefore under the control of the ER stress sensor element.

The ER stress sensor element can be inserted into any suitable vector, such as an episomal, centromeric or integrative plasmid. The vector may be a yeast vector including a cosmid or a yeast artificial chromosome.

Expression of the reporter element can be proportional to the level of ER stress to which the cell of the invention is subjected.

The exogenous gene can encode any one of the human disease proteins known to induce pathological conditions which are, at least partially, associated with induction of ER stress.

An exogenous gene may be a foreign DNA sequence i.e. a DNA sequence encoding a protein not endogenously present in a particular cell, or a DNA sequence that is endogenous to a particular cell but is not normally present in that location in the genome or is not normally under control of the same regulatory sequences or a DNA sequence that is endogenous to a particular cell but that has been changed in order to carry a disease-causing mutation.

The exogenous gene may encode a protein including, but not limited to, Aβ peptides (plaques); atrial natriuretic factor, CFTR (cystic fibrosis transmembrane regulator), insulin receptor, PS1 (Presenilin 1), transthyretin (TTR—over 45 mutants, whole or fragments), apolipoprotein AI, SOD1 (superoxide dismutase 1), LDLR (low density lipoprotein receptor), gelsolin, tau (wild-type or mutant), β-galactosidase, β2-microglobulin, L2-microglobulin, cystatin c, lysozyme, fibrinogen α-A chain, apolipoprotein AI, apolipoprotein AII, FAH, Htt (huntingtin), immunoglobulin light chain, insulin, calcitonin, α-synuclein (wild-type or mutant), parkin, PLP1 (proteolipid protein 1), lg light chains (whole or fragments), serum amyloid A (whole or 76-residue fragment), hemoglobin, androgen receptor, ataxies, PrP (prion protein), APP (amyloid precursor protein), amylin, PERK, WFS1 or A1AT (alpha 1-antitrypsin). The exogenous gene may also encode any other protein with a mutation known to cause human disease or a protein with any combination of such mutations.

The transthyretin gene may comprise i) the nucleic acid sequence set forth in SEQ ID NO:2, a nucleic sequence that is more than 95% homologous thereto or to its DNA complement or counterpart RNA sequence, a variant, fragment or the complementary strand thereof, ii) a nucleic acid sequence, especially DNA or RNA, which hybridises to the DNA sequence of SEQ ID NO:2, a nucleic acid sequence that is more than 95% homologous thereto or a variant or fragment thereof or iii) a nucleic acid sequence, especially DNA or RNA, which, but for the degeneracy of the genetic code, would hybridise to the DNA sequence of SEQ ID NO:2.

The transthyretin gene according to the invention may also encode a protein comprising a mutation from valine to methionine at position 50 or a protein comprising a mutation from leucine to proline at position 75 of the protein encoded by SEQ ID NO:2. The mutation at position 50 corresponds to a change of the codon GTG to the codon ATG in the DNA sequence and the mutation at position 75 corresponds to a change of the codon CTG to the codon CCG in the DNA sequence.

These aspects of the invention extend to a transthyretin gene comprising a nucleic acid sequence that is at least 96%, 97%, 98% or 99% homologous with the DNA sequence of SEQ ID NO:2 or with its DNA complement or a counterpart RNA sequence.

The tau gene may comprise i) the nucleic acid sequence set forth in SEQ ID NO:3, a nucleic sequence that is more than 95% homologous thereto or to its DNA complement or counterpart RNA sequence, a variant, fragment or the complementary strand thereof, ii) a nucleic acid sequence, especially DNA or RNA, which hybridises to the DNA sequence of SEQ ID NO:3, a nucleic acid sequence that is more than 95% homologous thereto or a variant or fragment thereof or iii) a nucleic acid sequence, especially DNA or RNA, which, but for the degeneracy of the genetic code, would hybridise to the DNA sequence of SEQ ID NO:3.

The tau gene according to the invention may also encode a protein comprising a mutation from proline to serine, which corresponds to a change from cytosine to thymine at position 727 of SEQ ID NO:3. The invention further includes a protein comprising a mutation from proline to leucine, which corresponds to a change from cytosine to thymine at position 728 of SEQ ID NO:3. The invention also includes a protein comprising a deletion of the residue lysine, which corresponds to a deletion of the residues adenine, adenine and guanine (AAG) at positions 664-666 of SEQ ID NO:3. The tau gene of the invention also includes a protein comprising a mutation from glycine to valine, corresponding to a change from guanine to thymine at position 641 of SEQ ID NO:3, a mutation from proline to leucine, which corresponds to a change from cytosine to thymine at position 728 of SEQ ID NO:3, a mutation from valine to methionone, which corresponds to a mutation from guanine to adenine at position 835 of SEQ ID NO:3 and a mutation from arginine to tryptophan, which corresponds to a mutation from cytosine to thymine at position 1042 of SEQ ID NO:3.

This aspect of the invention extends to a tau gene comprising a nucleic acid sequence that is at least 96%, 97%, 98% or 99% homologous with the DNA sequence of SEQ ID NO:3 or with its DNA complement or a counterpart RNA sequence.

The CFTR gene may comprise i) the nucleic acid sequence set forth in SEQ ID NO:4, a nucleic sequence that is more than 95% homologous thereto or to its DNA complement or counterpart RNA sequence, a variant, fragment or the complementary strand thereof, ii) a nucleic acid sequence, especially DNA or RNA, which hybridises to the DNA sequence of SEQ ID NO:4, a nucleic acid sequence that is more than 95% homologous thereto or a variant or fragment thereof or iii) a nucleic acid sequence, especially DNA or RNA, which, but for the degeneracy of the genetic code, would hybridise to the DNA sequence of SEQ ID NO:4.

The CFTR gene according to the invention may also encode a protein comprising a mutation that is a deletion of the residue phenylalanine at position 508 of the protein encoded by SEQ ID NO:4. In a further embodiment, the CFTR gene may also encode a mutation from glycine to aspartic acid at position 551, a protein comprising a mutation from arginine to threonine at position 560 or a protein comprising a mutation from alanine to glutamic acid as position 561 of the protein encoded by SEQ ID NO:4.

This aspect of the invention extends to a CFTR gene comprising a nucleic acid sequence that is at least 96%, 97%, 98% or 99% homologous with the DNA sequence of SEQ ID NO:4 or with its DNA complement or a counterpart RNA sequence.

Expression of the exogenous gene generates a condition of ER stress in the cells of the invention, which results in all or part of the features of the disease associated with the expression of that specific protein occurring within the cell system. The ER stress sensor element is activated in response to the ER stress that is induced by expression of the exogenous gene. In this way, the cell of the invention can represent a model system of any particular ER stress-related disease or disorder depending on the exogenous gene that is expressed.

This cell allows for the targeted identification of compounds with potential therapeutic application. Expression of the exogenous gene (the disease protein) can be achieved by cloning of the desired cDNA into an appropriate vector using conventional recombinant DNA technology, followed by introduction into the modified cell system.

The cells according to the invention can additionally comprise at least one promoter. The promoter can be operatively linked to the exogenous gene encoding a protein that induces ER stress. The promoter may be constitutive, inducible and/or specific for expression in a cell of the invention. Preferably, the promoter drives expression of the exogenous gene encoding a protein that induces ER stress. In one embodiment, the promoter is an inducible gal promoter.

ER stress refers to an imbalance between the demand that expression of proteins makes on the ER and the actual folding capacity of the ER to meet that demand. A response that counteracts ER stress has been termed "unfolded protein response" (UPR).

The second aspect of the invention provides a method of screening a candidate agent for its ability to modulate ER stress comprising the steps of:
a) contacting a cell of the first aspect of the invention with a candidate agent and
b) determining the effect of the candidate agent on the level of expression of the reporter element.

In one embodiment, the screen includes the exogenous gene of the cell being expressed Determining the effect of the candidate agent on the level of expression of the reporter element can be done, for example, by comparing expression of the reporter element of the cell that has been contacted with the candidate agent with expression of a reporter element in a second cell of the first aspect of the invention, that has not been contacted with the candidate agent, and wherein the exogenous gene of the second cell is also expressed. Alternatively, expression of the reporter element of the cell that has been contacted with the candidate agent could be compared with the expression of a reporter element in a cell that has been contacted with an agent whose effect is known.

A candidate agent is any substance to be tested to determine any ability to increase or decrease the ER stress in a cell of the invention. These candidate agents include known and unidentified compounds isolated from microorganisms, animals, plants or any other living organisms which are used to extract possible effective modulator agents. A candidate agent can be a small molecule including natural or synthetic molecules, including peptidomimetics, peptides or polypeptides or fragments thereof including binding peptides or polypeptides, antibodies or fragments thereof, ribozymes and nucleic acids including double stranded or single stranded DNA or RNA, a modification or derivative thereof, for example, antisense oligonucleotides, aptamers, siRNAs and ribozymes.

A candidate agent can be part of a library that is being screened, for example, a chemical library, a natural product library (including unidentified compounds isolated from microorganisms, animals, plants or any other living organisms which are used to extract possible effective modulator agents), a phage display library, a cDNA library or a siRNA library.

Quantification of the reporter element expression can be carried out using spectrophotometry, fluorimetry, luminescence, quantitative RT-PCR, Northern blotting, Western blotting, or any other detection method known by a skilled person.

Modulation of ER stress is reflected by an increase or decrease in reporter element expression/activity. Modulation of ER stress can be represented by a decrease in reporter element expression that is caused by a decrease in ER stress. A candidate agent that decreases ER stress may have direct potential for treating ER stress diseases or disorders.

Alternatively, modulation of ER stress can be represented by an increase in reporter element expression that is caused by an increase in ER stress. A candidate agent that increases ER-stress can be applied in treating infectious diseases, such as fungal infections, bacteria and/or other parasite infections provided the agent increases ER stress in the disease causing organism and not the host. A candidate agent that increases ER stress may also have indirect potential for treating ER stress diseases or disorders. For example, a siRNA candidate agent that results in an increase in ER stress may be used to identify a gene that plays a role in the pathway of the ER stress disease that is being represented in the cell and thus may identify a target for other candidate agents and/or screens.

Once a candidate agent has been identified as an ER stress modulator, specificity of the modulator to a particular stress-inducing condition (i.e. the disease/disorder that is associated with the exogenous gene encoding a protein that induces ER stress) will be evident by comparing the effect of the same compound in a condition of general chemical ER stress induction (e.g. tunicamycin or thapsigargin treatment).

Indeed, it can be important to be able to exclude compounds which act as general modulators of ER stress, as they can potentially interfere with the normal physiology of the cell and therefore may not be the best candidates for therapeutic applications.

As used herein, "contacting" the cell with a compound refers to exposing, incubating, touching, associating or making the compound accessible to the cell.

The methods of screening of the invention provide a system for measuring toxicity in the form of ER stress and thus does not only select for agents that reduce ER stress. ER stress is representative of cellular dysfunction such as aggregate formation, altered transcriptional regulation, mitochondrial dysfunction and impairment of the ubiquitin-proteasome system caused by protein conformational diseases. Incubation of the cell with a candidate agent that modulates ER stress should alleviate the cellular dysfunction and consequently lead to a measurable reduction in ER stress. Candidate agents may act anywhere along the pathway of mutant protein dysfunction, either upstream, downstream or at a level of the ER. Measurement of ER stress is a checkpoint for cellular dysfunction and reflects the general condition of the cell upon expression of a specific disease protein together with treatment with a candidate agent.

One of the advantages of the methods of screening of the invention is that, as discussed above, it measures toxicity in the form of ER stress. This type of screen has advantages of selecting both for compounds that interact with the protein expressed by the exogenous gene by also downstream or upstream targets. Furthermore, the simplicity of the screen means that it can be conducted relatively cheaply and quickly.

In the embodiment of the invention that uses a yeast cell for screening, a mammalian cell line, for example a human cell line, can be generated that can express the same exogenous gene as the cell of the invention and this can be used to verify candidate compounds obtained as a result of the screen using the yeast cell.

Efficacy of the candidate compounds can be determined by standard pharmaceutical procedures in this mammalian platform of ER stress conditions, e.g., for determining the LD50 (the dose that is lethal to 50% of the population) and the ED50 (the dose that is therapeutically effective in 50% of the population). The therapeutic index is the ratio between toxic and therapeutic effects and can be expressed as LD50/ED50. Preference will be given to compounds which exhibit large therapeutic indices.

The third aspect of the invention provides a candidate agent identified by a method of screening of the invention. The candidate agent selected by a screening method can be an activator or an inhibitor and/or a transcriptional modulator, a translational modulator, a folding modulator, a protein interaction modulator, a protein stability modulator, an aggregation modulator or any other modulator that ameliorates the cellular dysfunction caused by expression of the exogenous gene encoding a protein that induces ER stress. The candidate agents identified by a screening method of the invention can have potential use in medicine, biotechnology, veterinary, agriculture, industry, and any other field where application of ER stress modulators is applicable.

The fourth aspect of the invention provides a candidate agent identified by the method of screening of the invention for use in medicine. In one embodiment, the candidate agents are for use in treating ER stress-related diseases or disorders. An ER stress-related disease or disorder is a disease or disorder caused by or contributed to be ER stress levels. For example, Alzheimer's disease, atherosclerosis, atrial amyloidosis, cerebral ischemia, cystic fibrosis, diabetes mellitus, familial Alzheimer's disease, familial amyloid polyneuropathy I, familial amyloid polyneuropathy III, familial amyotrophic lateral sclerosis (FALS), familial hypercholestrolemia, Finnish hereditary systemic amyloidosis, frontotemporal dementias, GM1 gangliosidosis, haemodialysis-related amyloidosis, haemodialysis-related amyloidosis, hereditary cerebral amyloid angiopathy, hereditary non-neuropathic systemic amyloidosis, hereditary renal amyloidosis, hereditary tyrosinemia type I, Huntington's disease, immunoglobulin light chain amyloidosis, inflammation, injection-localised amyloidosis, medullary carcinoma of the thyroid, Parkinson's disease, Pelizaeus-Merzbacher disease, primary systemic amyloidosis, secondary systemic amyloidosis, senile systemic amyloidosis, sickle cell anemia, solid tumours, spinal and bulbar muscular atrophy, spinocerebellar ataxias, spongiform encephalopathy, sporadic inclusion body myositis, type II diabetes, viral infections, Wolcott-Rallison syndrome, Wolfram syndrome or Z alpha 1-antitrypsin deficiency.

The fifth aspect of the invention provides a method for treating ER stress-related diseases or disorders in a subject comprising the step of administering a candidate agent identified by the method of screening of the invention to the subject. The subject is in need of such treatment or might benefit from such treatment.

In one embodiment, more than one candidate agent identified by the method of the invention is administered to the subject. In a further embodiment, the candidate agents are administered simultaneously, separately or sequentially.

The term "treatment" is used herein to refer to any regimen that can benefit a human or non-human animal in need of such treatment or that might benefit from such treatment. The treatment may be in respect of an existing condition or may be prophylactic (preventative treatment). Treatment may include curative, alleviation or prophylactic effects.

More specifically, reference herein to "therapeutic" and "prophylactic" treatment is to be considered in its broadest context. The term "therapeutic" does not necessarily imply that a subject is treated until total recovery. Similarly, "prophylactic" does not necessarily mean that the subject will not eventually contract a disease condition.

Accordingly, therapeutic and prophylactic treatment includes amelioration of the symptoms of a particular condition or preventing or otherwise reducing the risk of developing a particular condition. The term "prophylactic" may be considered as reducing the severity or the onset of a particular condition. "Therapeutic" may also reduce the severity of an existing condition.

A therapeutically effective amount of a candidate agent identified by the method of screening of the invention is administered. The term "therapeutically effective amount" as used herein means an amount capable of reducing or treating an ER stress-related disease or disorder.

The candidate agent identified by the method of screening of the invention may be administered to a patient in need of treatment via any suitable route. The precise dose will depend upon a number of factors, including the precise nature of the form of a candidate agent identified by the method of screening of the invention to be administered.

The present invention is equally applicable to human and to veterinary medicine.

Route of administration may include; parenterally (including subcutaneous, intramuscular, intravenous, by means of, for example a drip patch), some further suitable routes of administration include (but are not limited to) oral (including buccal and sublingual), rectal, nasal, topical, infusion, vaginal, intradermal, intraperitoneally, intracranially, intrathecal and epidural administration or administration via oral or nasal inhalation, by means of, for example a nebuliser or inhaler, or by an implant.

The candidate agent identified by the method of screening of the invention can be deliverable as an injectable composition, is administered orally, or is administered to the lungs as an aerosol via oral or nasal inhalation.

For administration via the oral or nasal inhalation routes, preferably the candidate agent identified by the method of screening of the invention will be in a suitable pharmaceutical formulation and may be delivered using a mechanical form including, but not restricted to an inhaler or nebuliser device.

Further, where the oral or nasal inhalation routes are used, administration is by a SPAG (small particulate aerosol generator) may be used.

For intravenous injection, the candidate agent identified by the method of screening of the invention will be in the form of a parenterally acceptable aqueous solution which is pyrogen-free and has suitable pH, isotonicity and stability. Those of relevant skill in the art are well able to prepare suitable solutions using, for example, isotonic vehicles such as sodium chloride injection, Ringer's injection, Lactated Ringer's injection. Preservatives, stabilisers, buffers, antioxidants and/or other additives may be included, as required.

A candidate agent identified by the method of screening of the invention for oral administration may be in tablet, capsule, powder or liquid form. A tablet may comprise a solid carrier such as gelatin. Liquid compositions generally comprise a liquid carrier such as water, petroleum, animal or vegetable oils, mineral oil or synthetic oil. Physiological saline solution, dextrose or other saccharide solution or glycols such as ethylene glycol, propylene glycol or polyethylene glycol may be included.

The candidate agent may also be administered via microspheres, liposomes, other microparticulate delivery systems or sustained release formulations placed in certain tissues including blood. Suitable examples of sustained release carriers include semipermeable polymer matrices in the form of shared articles, e.g. suppositories or microcapsules. Implantable or microcapsular sustained release matrices include polylactides (U.S. Pat. No. 3,773,919; EP-A-0058481) copolymers of L-glutamic acid and gamma ethyl-L-glutamate (Sidman et al, Biopolymers 22(1): 547-556, 1985), poly (2-hydroxyethyl-methacrylate) or ethylene vinyl acetate (Langer et al, J. Biomed. Mater. Res. 15: 167-277, 1981, and Langer, Chem. Tech. 12:98-105, 1982).

Examples of the techniques and protocols mentioned above and other techniques and protocols which may be used in accordance with the invention can be found in Remington's Pharmaceutical Sciences, 18th edition, Gennaro, A. R., Lippincott Williams & Wilkins; 20th edition (Dec. 15, 2000) ISBN 0-912734-04-3 and Pharmaceutical Dosage Forms and Drug Delivery Systems; Ansel, H. C. et al. 7th Edition ISBN 0-683305-72-7 the entire disclosures of which is herein incorporated by reference.

The actual amount administered, and rate and time-course of administration, will depend on the nature and severity of what is being treated. Prescription of treatment, e.g. decisions on dosage etc, is ultimately within the responsibility and at the discretion of general practitioners and other medical doctors, and typically takes account of the disorder to be treated, the condition of the individual patient, the site of delivery, the method of administration and other factors known to practitioners.

The optimal dose can be determined by physicians based on a number of parameters including, for example, age, sex, weight, severity of the condition being treated, the active ingredient being administered and the route of administration.

The sixth aspect of the invention provides a method of producing a cell according to the first aspect of the invention comprising introducing a nucleotide sequence encoding an ER stress sensor element, a nucleotide sequence encoding a reporter element and a nucleotide sequence encoding an exogenous gene into a cell. Thus, the cell is transformed. In one embodiment the nucleotide sequence encoding an ER stress sensor element and a nucleotide encoding a reporter element are introduced into the cell on the same vector and the nucleotide sequence encoding an exogenous gene is introduced into the cell on a different vector. In a further embodiment, all the nucleotide sequences are introduced into the cell on the same vector.

The vectors carrying the desired nucleic acid molecules can be integrated into the host cell genome, either through homologous recombination into a specific genomic locus or through non-homologous recombination into any site of the host cell genome.

The transformed cell can be validated by growing the cell in the presence of the protein, which the exogenous gene encodes for. Expression of the report element indicates successful transformation.

The invention also provides a vector comprising a nucleotide sequence encoding an ER stress element, a nucleotide sequence encoding a reporter element and a nucleotide sequence encoding a gene that induces ER stress.

Preferred features for the second and subsequent aspects of the invention are as for the first aspect of the invention mutatis mutandis.

Throughout the specification, unless the context demands otherwise, the terms 'comprise' or 'include', or variations such as 'comprises' or 'comprising', 'includes' or 'including' will be understood to imply the inclusion of a stated integer or group of integers, but not the exclusion of any other integer or group of integers. In contrast, the term "consisting of" means the inclusion of a stated integer or group of integers, to the exclusion of any other integer or group of integers. It envisaged that where the term "comprising" is used, it is also possible to use the term "consisting of".

The invention will now be further described by reference to the following Examples, which are provided for the purposes of illustration only and are not to be construed as being limiting to the invention.

EXAMPLES

Example 1

Yeast Strain and Transformation

In this study, we used the yeast strain Y00000 (MATa; his3Δ1; leu2 Δ0; met15 Δ0; ura3 Δ0) as a host cell for all the constructs and for yeast chromosomal DNA isolation. Transformation of the yeast cells was performed accordingly to the LiAc method (Gietz, D., A. St. Jean, R. A. Woods and R. H. Schiestl. 1992, *Nucleic Acids Res.* 20: 1425).

Construction of the ER Sensor Reporter Plasmid

A 141 bp fragment of the yeast KAR2 promoter (SEQ ID NO:1) was amplified by PCR. The amplified fragment spans from nucleotides −136 to +5 (with reference to the transcription initiation site at +1) and comprehends one UPRE and two putative TATA sequences. The primers used for PCR amplification contained restriction sites in the extremities so that the amplified DNA fragment was digested and cloned into the multiple cloning site of the pGRU2 vector, immediately upstream of the coding sequence of YEGFP.

In the yeast *Saccharomyces cerevisiae* the Bip protein is the product of the KAR2 gene. Induction of ER stress by the presence of an UPRE induces the production of Bip through the binding of HAC1 protein to a cis-acting UPRE present in the promoter of the KAR2 gene. Cloning of the KAR2 UPRE and basal promoter upstream the YEGFP coding sequence allows the production of green fluorescence signal as a measure of ER stress.

Generation of the ER Stress-Reporter Yeast Strain

The ER stress sensor plasmid was transformed in the strain Y00000 and validation of this sensor was conducted by growing the transformed strain in the presence of tunicamycin. The induction of ER stress was quantified by measurement of the green fluorescence signal in comparison to the same cells grown in the absence of tunicamycin. The generated strain was named DISAGGREGATOR I (DGI).

Cloning of the Human Tau Mutants

The coding sequence of the human Tau protein (SEQ ID NO:3) was obtained from the IMAGE consortium and subcloned into the multiple cloning site of a yeast episomal vector, under the control of the Gal1 promoter. Tau mutants (P301L, P301S, ΔK280 and Tetra mutant) were generated by site-directed mutagenesis. After transformation of these constructs, expression of the Tau isoforms was induced by growing the cells on 2% galactose. Specific detection of the Tau protein and assessment of the correct molecular weight was verified by Western blotting using a polyclonal antibody against Tau protein.

Generation of the Yeast Platform for the Identification of Modulators of ER Stress Induced by the Expression of Mutant Tau The episomal plasmids containing the wild type and mutant Tau sequences under the control of the Gal1 promoter were transformed into the ER stress-reporter yeast strain.

The generated strains were named DISAGGREGATOR I—TAUWT (DGI-TAUWT), DISAGGREGATOR I—TAUP301L (DGI-TAUP301L), DISAGGREGATOR I—TAUP301S (DGI-TAUP301S), DISAGGREGATOR I—TAUΔK280 (DGI-TAUΔK280) and DISAGGREGATOR I—TAUTETRA (DGI-TAUTETRA). ER stress induction upon expression of the Tau proteins was validated by growing the cells on 2% galactose and determining the increase in the green fluorescence signal.

Screening Assay Validation

Screening was conducted with a DGI-TAUP301L yeast cell expressing the mutant TAU-P301L protein under the control of GAL1 promoter and containing the ER stress sensor reporter plasmid with GFP as reporter, described above in the "Construction of the ER sensor reporter plasmid" section. Expression of TAUP301L resulted in a cytotoxic response that triggers ER stress and hence fluorescence by the reporter. The resulting fluorescent signal was normalised to cell density and the normalised fluorescence was used as a direct measure of ER stress level in the cells.

A commercial library containing 50 080 small molecules was screened along with 5 dipeptide molecules from an academic collaboration and 208 extracts from a proprietary natural extract collection. Active compounds, with the potential to modulate the deleterious effects of TAU-P301L expression, were identified by their ability to decrease normalised fluorescence, without influencing growth. Growth was determined by measuring optical density (OD) of a culture.

DGI-TAUP301L cells were dispensed into 96-well plates on minimum medium containing 2% galactose to fully express the mutant protein, together with 10 µM candidate compound. All liquid handing steps were performed using a Janus Automated Workstation (Perkin Elmer). Plates were incubated for 2 days at 30° C. under shaking in a Liconic STX40 Automated Incubator. Growth and fluorescence were monitored with a Victor 3V microplate reader (PE). In parallel, cells were cultivated in the same conditions without compounds or with different control compounds.

Compounds already proven to be capable of alleviating ER stress were chosen as controls. Molecules directly active against the TAU-P301L protein are not presently available but ER stress inhibitors are already present on the market, such as chemical chaperones. Chemical chaperones (e.g. choline or DMSO) enhance the adaptive capacity of the ER and their addition to the culture medium results in a decreased ER stress response. Another commonly used compound is salubrinal, identified as an inhibitor of phosphatases that act on the eukaryotic translation initiation factor 2 subunit (eIF2α). The resulting maintenance of protein phosphorylation results in enhanced protection from the adverse effects of ER stress, mainly because eIF2α phosphorylation causes a halt in protein synthesis. These compounds were used to validate the cellular response of our screening and estimate the activity of the screened compounds.

Example 2.1

Effect of DMSO

DGI-TAUP301L cells were pre-grown on a mixture of 2% galactose until reaching early exponential phase (OD=1-2). The cells were washed three times with water and then resuspended at 0.1 OD in selective medium containing 2% galactose, in order to fully activate TAU-P301L expression. Cells were dispensed into 96-well plates and 4 µL DMSO were added to the desired wells, to a final concentration of 2%. In parallel, DMSO was not added to control wells. Growth and fluorescence were monitored for 2 days at 30° C. under agitation. FIG. 5 illustrates the results.

The amount of DMSO added to the wells (i.e. 4 µl per well) was based on the amount generally used in the literature to achieve alleviation of ER stress.

Example 2.2

Effect of Choline

Figure 6:
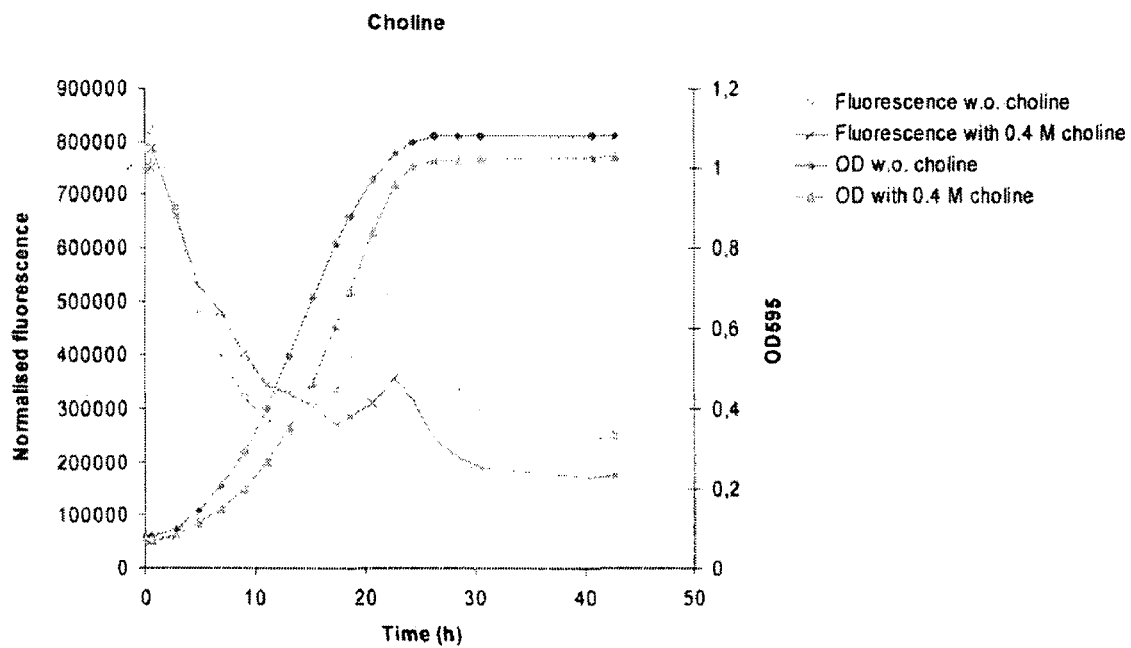
FIG. 6 illustrates growth and fluorescence signal of DGI-TAUP301L cells on minimum medium with 2% galactose with or without 0.4 M choline.

DGI-TAUP301L cells were pre-grown on a mixture of 2% galactose until reaching early exponential phase (OD=1-2). The cells were washed once with water and then resuspended at 0.1 OD in selective medium containing 2% galactose, in order to fully activate TAU-P301L expression. Cells were dispensed into 96-well plates and choline was added to the desired wells, to a final concentration of 0.4 M. In parallel, choline was not added to the control wells. Growth and fluorescence were monitored for 2 days at 30° C. under agitation. FIG. 6 illustrates the results.

The amount of choline added to the wells (i.e. to a final concentration of 0.4M per well) was based on the amount generally used in the literature to achieve alleviation of ER stress.

Example 2.3

Effect of Salubrinal

Figure 7:
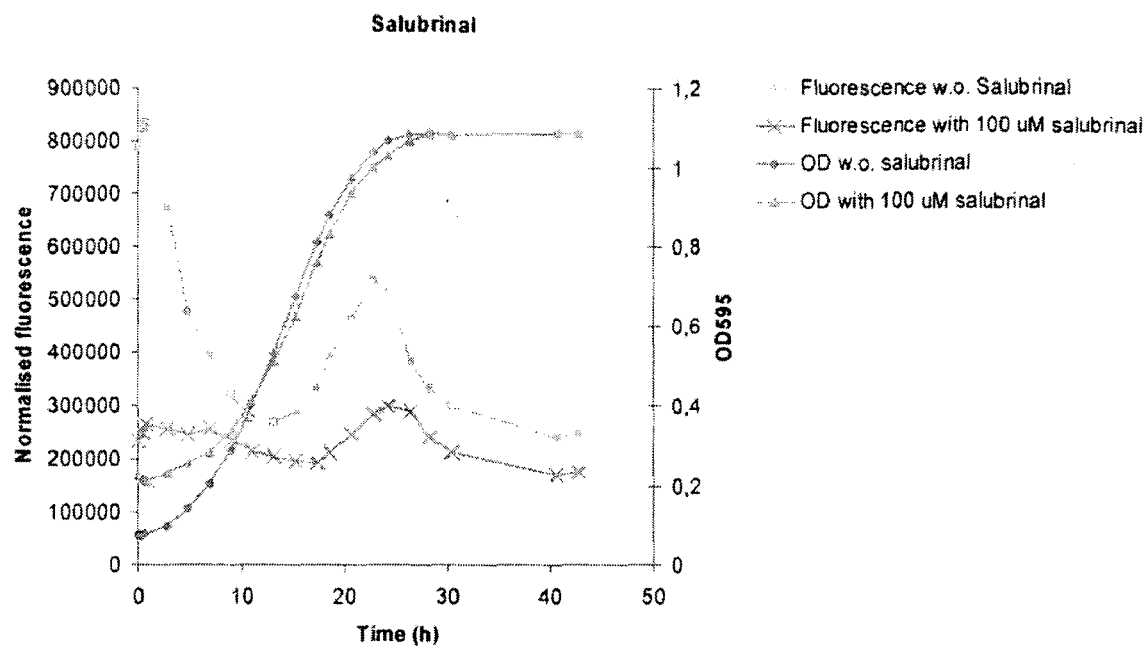
FIG. 7 illustrates growth and fluorescence signal of DGI-TAUP301L cells on minimum medium with 2% galactose with or without 100 µM salubrinal.

DGI-TAUP301L cells were pre-grown on a mixture of 2% galactose until reaching early exponential phase (OD=1-2). The cells were washed once with water and then resuspended at 0.1 OD in selective medium containing 2% galactose, in order to fully activate TAU-P301L expression. Cells were dispensed into 96-well plates and salubrinal was added to the desired wells, to a final concentration of 100 µM. In parallel, salubrinal was not added to the control wells. Growth and fluorescence were monitored for 2 days at 30° C. under agitation. FIG. 7 illustrates the results.

The amount of salbrinal added to the wells (i.e. to a final concentration of 100 nM per well) was based on the amount generally used in the literature to achieve alleviation of ER stress.

Example 2.4

Effect of New Compound DGI-T2008A

Figure 8:
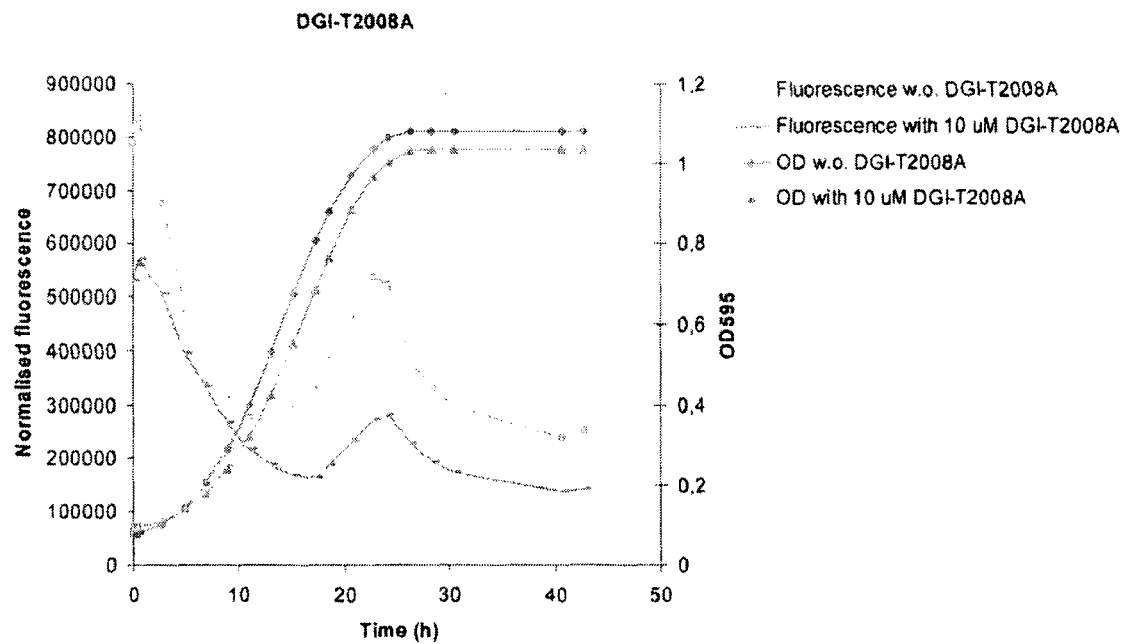
FIG. 8 illustrates growth and fluorescence signal of DGI-TAUP301L cells on minimum medium with 2% galactose with or without 10 µM DGI-T2008A.

DGI-TAUP301L cells were pre-grown on a mixture of 2% galactose until reaching early exponential phase (OD=1-2). The cells were washed once with water and then resuspended at 0.1 OD in selective medium containing 2% galactose, in order to fully activate TAU-P301L expression. Cells were dispensed into 96-well plates and compound DGI-T2008A was added to the desired wells, to a final concentration of 10 µM. In parallel, DGI-T2008A was not added to the control wells. Growth and fluorescence were monitored for 2 days at 30° C. under agitation. FIG. 8 illustrates the results.

Figure 9:
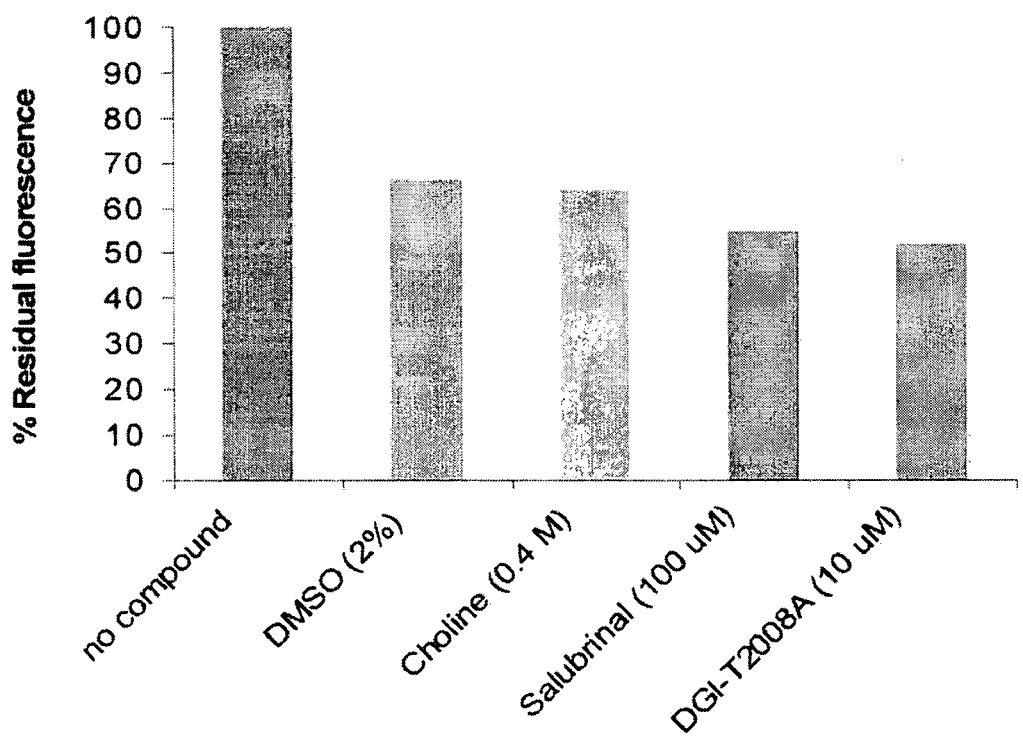
FIG. 9 illustrates action of new compound DGI-T2008A on ER stress signal in DGI-TAUP301L cells compared to control compounds.

Compound DGI-T2008A was able to reduce the ER stress signal by almost 50% at a concentration of 10 µM (FIGS. 8 and 9). Such a reduction was only achieved by using a ten-fold concentration of salubrinal (100 µM) (see FIG. 9). Choline and DMSO resulted in only a 35% reduction of ER stress even when used at a much higher concentration than the test compound. These results illustrate the robustness of the present invention for the screening of ER stress alleviating compounds.

Generation of Stable Mammalian Cell Lines Expressing Wild Type and Mutant Tau and Assessment of ER Stress Modulation by Candidate Compounds SH-SY5Y human neuroblastoma cells (ATCC) were grown on DMEM supplemented with 10% foetal calf serum. The coding sequences of human Tau (wild type and mutants) were subcloned into the pcDNA3 mammalian expression vector, which was linearized and transfected into SH-SY5Y cells. After growth in G418 selective medium, pools of resistant cells were obtained. Expression of the Tau protein and assessment of the correct molecular weight was verified for each pool by Western blotting using a polyclonal antibody against Tau. Induction of ER stress upon Tau expression was verified by detecting an increased production of the ER stress protein markers Bip and ATF4 by Western blotting. As a control, a pool of cells transfected with the empty vector was generated and used for all the subsequent experiments. For the validation of hits from the DGI-TAUP301L screening, SH-SY5Y cells stably expressing Tau P301L will be incubated in the presence and absence of the candidate compounds and modulation of ER stress will be evaluated by the increase/decrease in the protein level of ER stress markers.

Example 2

Yeast Strain and Transformation

In this study, we used the yeast strain Y00000 (MATa; his3Δ1; leu2 Δ0; met15 Δ 0; ura3 Δ0) as host cell for all the constructs and for yeast chromosomal DNA isolation. Transformation of the yeast cells was performed accordingly to the LiAc method (Gietz, D., A. St. Jean, R. A. Woods and R. H. Schiestl. 1992, *Nucleic Acids Res.* 20: 1425).

Construction of the ER Sensor Reporter Plasmid

A 141 bp fragment of the yeast KAR2 promoter (SEQ ID NO:1) was amplified by PCR. The amplified fragment spans from nucleotides −136 to +5 (with reference to the transcription initiation site at +1) and comprehends one UPRE and two putative TATA sequences. The primers used for PCR amplification contained restriction sites in the extremities so that the amplified DNA fragment was digested and cloned into the multiple cloning site of the pGRU2 vector, immediately upstream of the coding sequence of YEGFP (yeast enhanced green fluorescent protein).

In the yeast *Saccharomyces cerevisiae* the Bip protein is the product of the KAR2 gene. Induction of ER stress by any of the above mentioned conditions induces the production of Bip through the binding of HAC1 protein to a cis-acting UPRE present in the promoter of the KAR2 gene. Cloning of the KAR2 UPRE and basal promoter upstream the YEGFP coding sequence allows the production of green fluorescence signal as a measure of ER stress.

Generation of the ER Stress-Reporter Yeast Strain

The ER stress sensor plasmid was transformed in the strain Y00000 and validation of this sensor was conducted by growing the transformed strain in the presence of tunicamycin. The induction of ER stress was quantified by measurement of the green fluorescence signal in comparison to the same cells grown in the absence of tunicamycin. The generated strain was named DISAGGREGATOR I (DGI).

Cloning of the Human TTR Mutants

A 444 bp fragment containing the coding region of the human TTR gene (SEQ ID 2) was amplified by PCR using cDNA from human HepG2 cells as template. The primers used for PCR amplification contained restriction sites in the extremities so that the amplified DNA fragment was digested and cloned into the multiple cloning site of an yeast episomal vector, under the control of the GAL1 promoter. TTR mutants (V30M and L55P) were generated by site-directed mutagenesis. After transformation of the constructs, expression of TTR mutants was induced by growing the cells on 2% galactose. Specific detection of the TTR protein and assessment of correct molecular weight were verified by western blotting using a polyclonal antibody against TTR.

Generation of the Yeast Platform for the Identification of Modulators of ER Stress Induced by the Expression of Mutant TTR The episomal plasmids containing the wild type and mutant TTR sequences under the control of the Gal1 promoter were transformed into the ER stress-reporter yeast strain. ER stress induction upon expression of the TTR isoforms was validated by growing the cells on 2% galactose and determining the increase in the green fluorescence signal.

The generated strains were named DISAGGREGATOR I—TTRWT (DGI-TTRWT), DISAGGREGATOR I—TTRV30M (DGI-TTRV30M) and DISAGGREGATOR I—TTRL55P (DGI-TTRL55P).

Screening Assay Validation

Screening was conducted using the DGI-TTR V30M yeast cell expressing the mutant TTR V30M protein under the control of GAL1 promoter and containing the ER stress sensor reporter plasmid with GFP as reporter, as described above in the "Construction of the ER sensor reporter plasmid" section. Expression of TTR V30M results in a cytotoxic response that triggers ER stress and hence fluorescence by the reporter. The resulting fluorescent signal is normalised to cell density and the normalised fluorescence is used as a direct measure of ER stress level in the cells. Active compounds, with the potential to modulate the deleterious effects of TTR V30M expression, are identified by their ability to decrease normalised fluorescence, without influencing growth.

DGI-TTR V30M cells were cultivated on minimum medium containing 2% galactose to fully express the mutant protein, together with 10 μM of candidate compound. All liquid handing steps were performed using a Janus Automated Workstation (Perkin Elmer). Plates were incubated for 2 days at 30° C. under shaking in a Liconic STX40 Automated Incubator. Growth and fluorescence were monitored with a Victor 3V microplate reader (PE). In parallel, cells were cultivated in the same conditions without candidate compounds.

Figure 10:
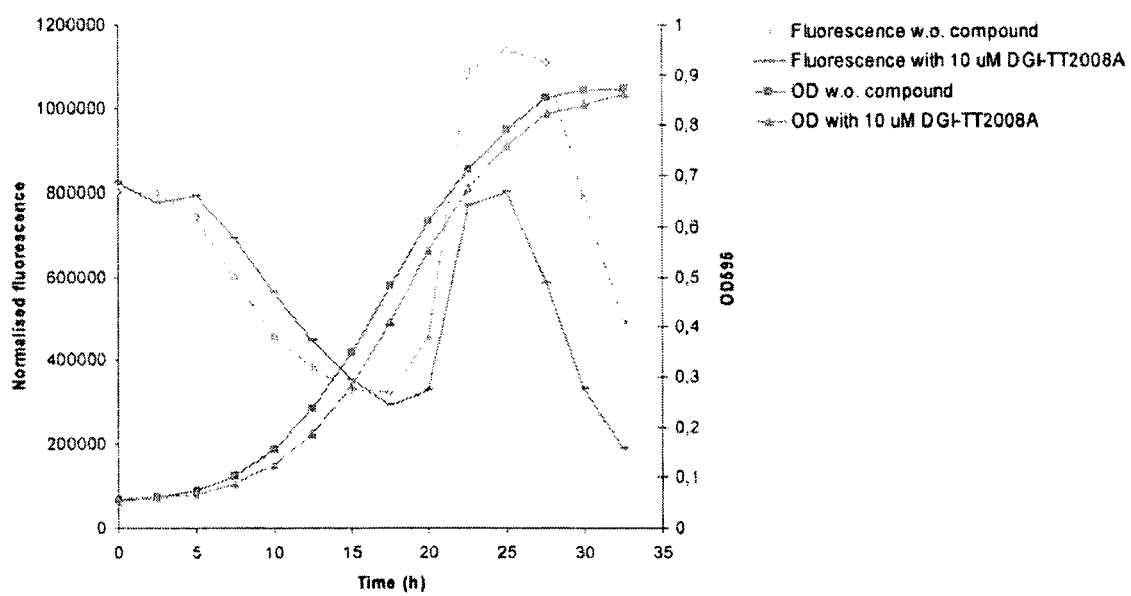
FIG. 10 illustrates growth and fluorescence signal of DGI-TTR V30M cells on minimum medium with 2% galactose with or without 10 µM DGI-TT2008A.

From a small molecule library, compound DGI-TT2008A was found to reduce ER stress induced by the mutant TTR V30M protein (FIG. 10).

Compound DGI-TT2008A was able to reduce the ER stress signal by almost 25% at a final concentration of 10 μM. These results illustrate the efficiency of the present invention for the screening of ER stress induced by the mutant TTR V30M protein. Furthermore, these results validate the versatility of the invention for different mutant proteins.

Generation of a Stable Mammalian Cell Line Expressing Mutant TTR and Assessment of ER Stress Modulation by Candidate Compounds HepG2 human hepatocyte cells (ATCC) were grown on RMPI 1640 supplemented with 10% foetal calf serum. The coding sequences of human TTR (wild type and mutants) were subcloned into the pcDNA3 mammalian expression vector, which was linearized and transfected into HepG2 cells. After growth in G418 selective medium, pools of resistant cells were obtained. Expression of TTR protein and assessment of the correct molecular weight were verified by western blotting using a polyclonal antibody against TTR. Induction of ER stress upon TTR expression was verified by detecting an increased production of the ER stress protein markers Bip and ATF4 by western blotting. As a control, a pool of cells transfected with the empty vector was generated and used for all the subsequent experiments. For the validation of hits from the DGI-TTRV30M screening, HepG2 cells stably expressing TTR V30M will be incubated in the presence and absence of the candidate compound and modulation of ER stress will be evaluated by the increase/decrease in the protein level of ER stress markers.

Example 3

Yeast Strain and Transformation

In this study, we used the yeast strain Y00000 (MATa; his3Δ1; leu2 Δ0; met15 Δ 0; ura3 Δ0) as host cell for all the constructs and for yeast chromosomal DNA isolation. Transformation of the yeast cells was performed accordingly to the LiAc method (Gietz, D., A. St. Jean, R. A. Woods and R. H. Schiestl. 1992, *Nucleic Acids Res.* 20: 1425).

Construction of the ER Sensor Reporter Plasmid

A 141 bp fragment of the yeast KAR2 promoter (SEQ ID NO:1) was amplified by PCR. The amplified fragment spans from nucleotides −136 to +5 (with reference to the transcription initiation site at +1) and comprehends one UPRE and two putative TATA sequences. The primers used for PCR amplification contained restriction sites in the extremities so that the amplified DNA fragment was digested and cloned into the multiple cloning site of the pGRU2 vector, immediately upstream of the coding sequence of YEGFP (yeast enhanced green fluorescent protein).

In the yeast *Saccharomyces cerevisiae* the Bip protein is the product of the KAR2 gene. Induction of ER stress by any of the above mentioned conditions induces the production of Bip through the binding of HAC1 protein to a cis-acting UPRE present in the promoter of the KAR2 gene. Cloning of the KAR2 UPRE and basal promoter upstream the YEGFP coding sequence allows the production of green fluorescence signal as a measure of ER stress.

Generation of the ER Stress-Reporter Yeast Strain

The ER stress sensor plasmid was transformed in the strain Y00000 and validation of this sensor was conducted by growing the transformed strain in the presence of tunicamycin. The induction of ER stress was quantified by measurement of the green fluorescence signal in comparison to the same cells grown in the absence of tunicamycin. The generated strain was named DISAGGREGATOR I (DGI).

Cloning of the Human CFTR Mutants

A 4720 bp fragment containing the coding region of the wild type human CFTR gene (SEQ ID NO:4) was subcloned from the pNUT vector (Tabcharani J A, Chang X B, Riordan J R, Hanrahan J W. Nature. 1991; 352 (6336):628-31) into the multiple cloning site of an yeast episomal vector, under the control of the GAL1 promoter. Additionally, four different CFTR mutants (ΔF508, G551D, R560T and A561E) were subcloned from pNUT into the yeast episomal vector. After transformation of the constructs, expression of CFTR isoforms was induced by growing the cells on 2% galactose. Specific detection of the CFTR protein and assessment of correct molecular weight were verified by western blotting using an antibody against CFTR.

Generation of the Yeast Platform for the Identification of Modulators of ER Stress Induced by the Expression of Mutant CFTR The episomal plasmids containing the wild type and mutant CFTR sequences under the control of the Gal1 promoter were transformed into the ER stress-reporter yeast strain. ER stress induction upon expression of the CFTR proteins was validated by growing the cells on 2% galactose and determining the increase in the green fluorescence signal.

The generated strains were named DISAGGREGATOR I—CFTRWT (DGI-CFTRWT), DISAGGREGATOR I—CFTRΔF508 (DGI-CFTRΔF508), DISAGGREGATOR I—CFTRG551D (DGI-CFTRG551D), DISAGGREGATOR I—CFTRR560T (DGI-CFTRR560T), and DISAGGREGATOR I—CFTRA561E (DGI-CFTRA561E).

The invention claimed is:

1. An isolated cell comprising an Endoplasmic Reticulum (ER) stress sensor element operably linked to a reporter element and comprising an exogenous gene encoding a protein that induces ER stress.

2. The cell as claimed in claim 1, wherein the cell is a eukaryotic cell.

3. The cell as claimed in claim 2, wherein the cell is a yeast cell.

4. The cell as claimed in claim 1, wherein the exogenous gene encodes an Aβ peptide (plaque); atrial natriuretic factor, CFTR (cystic fibrosis transmembrane regulator), insulin receptor, PS1 (Presenilin 1), transthyretin (over 45 mutants, whole or fragments), apolipoprotein AI, SOD1 (superoxide dismutase 1), LDLR (low density lipoprotein receptor), gelsolin, tau (wildtype or mutant), β-galactosidase, ß2-microglobulin, L2-microglobulin, cystatin c, lysozyme, fibrinogen α-A chain, apolipoprotein AI, apolipoprotein AII, Fumarylacetoacetate hydrolase (FAH), Htt (huntingtin), immunoglobulin light chain, insulin, calcitonin, α-synuclein (wildtype or mutant), parkin, PLP1 (proteolipid protein 1), Ig light chains (whole or fragments), serum amyloid A (whole or 76-residue fragment), hemoglobin, androgen receptor, ataxins, PrP (prion protein), APP (amyloid precursor protein), amylin, protein kinase RNA-like endoplasmic reticulum kinase (PERK), Wolfram protein (WFS1) or A1AT (alpha 1-antitrypsin).

5. The cell of claim 1, wherein the ER stress sensor element is a DNA sequence from an unfolded protein response element.

6. The cell of claim 1, wherein the ER stress sensor element is a DNA sequence from the karyogamy 2 (KAR2) unfolded protein response element.

7. A method of screening a candidate agent for its ability to inhibit ER stress comprising the steps of:
   a) contacting a cell of claim 1 with a candidate agent, and
   b) determining the effect of the candidate agent on the level of expression of the reporter element
   wherein a change in the level of expression of the reporter element is indicative of a candidate agent that inhibits ER stress.

8. A method of producing a cell of claim 1 comprising introducing a nucleotide sequence encoding an ER stress element operably linked to a reporter element and a nucleotide sequence encoding an exogenous gene into a cell.

9. The cell of claim 1, wherein the exogenous gene that induces ER stress is associated with a human disease.

* * * * *

UNITED STATES PATENT AND TRADEMARK OFFICE
CERTIFICATE OF CORRECTION

PATENT NO.        : 8,236,490 B2
APPLICATION NO.   : 12/663241
DATED             : August 7, 2012
INVENTOR(S)       : Christophe Roca et al.

Page 1 of 1

It is certified that error appears in the above-identified patent and that said Letters Patent is hereby corrected as shown below:

On the title page, item (73) Assignee, please delete "EM Biotecnologia S.A., Lisbon (PT)" and insert --Bioalvo -Serviços, Investigação e Desenvolvimento em Biotecnologia S.A., Lisboa, (PT)--.

Signed and Sealed this
Twenty-eighth Day of May, 2013

Teresa Stanek Rea
*Acting Director of the United States Patent and Trademark Office*

```
                        SEQUENCE LISTING

<160> NUMBER OF SEQ ID NOS: 4

<210> SEQ ID NO 1
<211> LENGTH: 141
<212> TYPE: DNA
<213> ORGANISM: Saccharomyces cerevisiae

<400> SEQUENCE: 1
cccgaggaac tggacagcgt gtcgaaaaag ttgcttttt atataaagga cacgaaaagg      60
gttctctgga agatataaat atggctatgt aattctaaag attaacgtgt tactgtttta     120 ctttttttaaa gtccccaaga g                                              141

<210> SEQ ID NO 2
<211> LENGTH: 444
<212> TYPE: DNA
<213> ORGANISM: Homo sapiens

<400> SEQUENCE: 2
atggcttctc atcgtctgct cctcctctgc cttgctggac tggtatttgt gtctgaggct      60
ggccctacgg gcaccggtga atccaagtgt cctctgatgg tcaaagttct agatgctgtc     120
cgaggcagtc ctgccatcaa tgtggccgtg catgtgttca gaaaggctgc tgatgacacc     180
tgggagccat ttgcctctgg gaaaaccagt gagtctggag agctgcatgg gctcacaact     240
```

-continued

| | |
|---|---|
| gaggaggaat tgtagaagg gatatacaaa gtggaaatag acaccaaatc ttactggaag | 300 |
| gcacttggca tctccccatt ccatgagcat gcagaggtgg tattcacagc caacgactcc | 360 |
| ggcccccgcc gctacaccat tgccgccctg ctgagcccct actcctattc caccacggct | 420 |
| gtcgtcacca atcccaagga atga | 444 |

<210> SEQ ID NO 3
<211> LENGTH: 1152
<212> TYPE: DNA
<213> ORGANISM: Homo sapiens

<400> SEQUENCE: 3

| | |
|---|---|
| atggctgagc cccgccagga gttcgaagtg atggaagatc acgctgggac gtacggttg | 60 |
| ggggacagga aagatcaggg gggctacacc atgcaccaag accaagaggg tgacacggac | 120 |
| gctggcctga agctgaaga agcaggcatt ggagacaccc ccagcctgga agacgaagct | 180 |
| gctggtcacg tgacccaagc tcgcatggtc agtaaaagca agacgggac tggaagcgat | 240 |
| gacaaaaaag ccaagggggc tgatggtaaa acgaagatcg ccacaccgcg gggagcagcc | 300 |
| cctccaggcc agaagggcca ggccaacgcc accaggattc cagcaaaaac ccgcccgct | 360 |
| ccaaagacac cacccagctc tggtgaacct ccaaaatcag gggatcgcag cggctacagc | 420 |
| agccccggct ccccaggcac tcccggcagc cgctcccgca cccgtccct tccaacccca | 480 |
| cccacccggg agcccaagaa ggtggcagtg gtccgtactc cacccaagtc gccgtcttcc | 540 |
| gccaagagcc gcctgcagac agcccccgtg cccatgccag acctgaagaa tgtcaagtcc | 600 |
| aagatcggct ccactgagaa cctgaagcac cagccgggag gcgggaaggt gcagataatt | 660 |
| aataagaagc tggatcttag caacgtccag tccaagtgtg gctcaaagga taatatcaaa | 720 |
| cacgtcccgg gaggcggcag tgtgcaaata gtctacaaac cagttgacct gagcaaggtg | 780 |
| acctccaagt gtggctcatt aggcaacatc catcataaac caggaggtgg ccaggtggaa | 840 |
| gtaaaatctg agaagcttga cttcaaggac agagtccagt cgaagattgg gtccctggac | 900 |
| aatatcaccc acgtccctgg cggaggaaat aaaaagattg aaacccacaa gctgaccttc | 960 |
| cgcgagaacg ccaaagccaa gacagaccac ggggcggaga tcgtgtacaa gtcgccagtg | 1020 |
| gtgtctgggg acacgtctcc acggcatctc agcaatgtct cctccaccgg cagcatcgac | 1080 |
| atggtagact cgccccagct cgccacgcta gctgacgagg tgtctgcctc cctggccaag | 1140 |
| cagggtttgt ga | 1152 |

<210> SEQ ID NO 4
<211> LENGTH: 4443
<212> TYPE: DNA
<213> ORGANISM: Homo sapiens

<400> SEQUENCE: 4

| | |
|---|---|
| atgcagaggt cgcctctgga aaaggccagc gttgtctcca aacttttttt cagctggacc | 60 |
| agaccaattt tgaggaaagg atacagacag cgcctggaat tgtcagacat ataccaaatc | 120 |
| ccttctgttg attctgctga caatctatct gaaaaattgg aaagagaatg ggatagagag | 180 |
| ctggcttcaa agaaaaatcc taaactcatt aatgcccttc ggcgatgttt tttctggaga | 240 |
| tttatgttct atggaatctt tttatattta ggggaagtca ccaaagcagt acagcctctc | 300 |
| ttactgggaa gaatcatagc ttcctatgac ccggataaca aggaggaacg ctctatcgcg | 360 |
| atttatctag gcataggctt atgccttctc tttattgtga ggacactgct cctacaccca | 420 |
| gccattttg gccttcatca cattggaatg cagatgagaa tagctatgtt tagtttgatt | 480 |

```
tataagaaga ctttaaagct gtcaagccgt gttctagata aaataagtat tggacaactt    540
gttagtctcc tttccaacaa cctgaacaaa tttgatgaag gacttgcatt ggcacatttc    600
gtgtggatcg ctcctttgca agtggcactc ctcatggggc taatctggga gttgttacag    660
gcgtctgcct tctgtggact tggtttcctg atagtccttg ccctttttca ggctgggcta    720
gggagaatga tgatgaagta cagagatcag agagctggga agatcagtga aagacttgtg    780
attacctcag aaatgattga aaatatccaa tctgttaagg catactgctg ggaagaagca    840
atggaaaaaa tgattgaaaa cttaagacaa acagaactga aactgactcg aaggcagcc    900 tatgtgagat acttcaatag ctcagccttc ttcttctcag ggttctttgt ggtgttttta    960
tctgtgcttc cctatgcact aatcaaagga atcatcctcc ggaaaatatt caccaccatc   1020
tcattctgca ttgttctgcg catggcggtc actcggcaat tccctgggc tgtacaaaca   1080 tggtatgact ctcttggagc aataaacaaa atacaggatt cttacaaaa gcaagaatat   1140 aagacattgg aatataactt aacgactaca gaagtagtga tggagaatgt aacagccttc   1200
tgggaggagg gatttgggga attatttgag aaagcaaaac aaaacaataa caatagaaaa   1260
acttctaatg gtgatgacag cctcttcttc agtaatttct cacttcttgg tactcctgtc   1320
ctgaaagata ttaatttcaa gatagaaaga ggacagttgt tggcggttgc tggatccact   1380
ggagcaggca agacttcact tctaatggtg attatgggag aactggagcc ttcagagggt   1440
aaaattaagc acagtggaag aatttcattc tgttctcagt tttcctggat tatgcctggc   1500
accattaaag aaaatatcat ctttggtgtt tcctatgatg aatatagata cagaagcgtc   1560
atcaaagcat gccaactaga agaggacatc tccaagtttg cagagaaaga caatatagtt   1620
cttggagaag gtggaatcac actgagtgga ggtcaacgag caagaatttc tttagcaaga   1680
gcagtataca aagatgctga tttgtattta ttagactctc cttttggata cctagatgtt   1740
ttaacagaaa aagaaatatt tgaaagctgt gtctgtaaac tgatggctaa caaaactagg   1800
attttggtca cttctaaaat ggaacattta aagaaagctg acaaaatatt aattttgcat   1860
gaaggtagca gctattttta tgggacattt tcagaactcc aaaatctaca gccagacttt   1920
agctcaaaac tcatgggatg tgattctttc gaccaattta gtgcagaaag aagaaattca   1980
atcctaactg agaccttaca ccgtttctca ttagaaggag atgctcctgt ctcctggaca   2040
gaaacaaaaa aacaatcttt taaacagact ggagagtttg gggaaaaaag gaagaattct   2100
attctcaatc caatcaactc tatacgaaaa ttttccattg tgcaaaagac tccccttacaa   2160 atgaatggca tcgaagagga ttctgatgag ccttagaga aaggctgtc cttagtacca   2220 gattctgagc agggagaggc gatactgcct cgcatcagcg tgatcagcac tggccccacg   2280
cttcaggcac gaaggaggca gtctgtcctg aacctgatga cacactcagt taaccaaggt   2340
cagaacattc accgaaagac aacagcatcc acacgaaaag tgtcactggc ccctcaggca   2400
aacttgactg aactgatat atattcaaga aggttatctc aagaaactgg cttgaaaata   2460
agtgaagaaa ttaacgaaga agacttaaag gagtgctttt ttgatgatat ggagagcata   2520
ccagcagtga ctcatggaa cacataccct cgatatatta ctgtccacaa gagcttaatt   2580
tttgtgctaa tttggtgctt agtaatttttt ctggcagagg tggctgcttc tttggttgtg   2640
ctgtggctcc ttgaaacac tcctcttcaa gacaaaggga atagtactca tagtagaaat   2700
aacagctatg cagtgattat caccagcacc agttcgtatt atgtgtttta catttacgtg   2760
ggagtagccg acactttgct tgctatggga ttcttcagag gtctaccact ggtgcatact   2820
ctaatcacag tgtcgaaaat tttacaccac aaaatgttac attctgttct tcaagcacct   2880
```

-continued

```
atgtcaaccc tcaacacgtt gaaagcaggt gggattctta atagattctc caaagatata    2940
gcaattttgg atgaccttct gcctcttacc atatttgact tcatccagtt gttattaatt    3000
gtgattggag ctatagcagt tgtcgcagtt ttacaaccct acatctttgt tgcaacagtg    3060
ccagtgatag tggcttttat tatgttgaga gcatatttcc tccaaacctc acagcaactc    3120
aaacaactgg aatctgaagg caggagtcca attttcactc atcttgttac aagcttaaaa    3180
ggactatgga cacttcgtgc cttcggacgg cagccttact ttgaaactct gttccacaaa    3240
gctctgaatt tacatactgc caactggttc ttgtacctgt caacactgcg ctggttccaa    3300
atgagaatag aaatgatttt tgtcatcttc ttcattgctg ttaccttcat ttccatttta    3360
acaacaggag aaggagaagg aagagttggt attatcctga ctttagccat gaatatcatg    3420
agtacattgc agtgggctgt aaactccagc atagatgtgg atagcttgat gcgatctgtg    3480
agccgagtct ttaagttcat tgacatgcca acagaaggta aacctaccaa gtcaaccaaa    3540
ccatacaaga atggccaact ctcgaaagtt atgattattg agaattcaca cgtgaagaaa    3600
gatgacatct ggccctcagg gggccaaatg actgtcaaag atctcacagc aaaatacaca    3660
gaaggtggaa atgccatatt agagaacatt tccttctcaa taagtcctgg ccagagggtg    3720
ggcctcttgg gaagaactgg atcagggaag agtactttgt tatcagcttt tttgagacta    3780
ctgaacactg aaggagaaat ccagatcgat ggtgtgtctt gggattcaat aactttgcaa    3840
cagtggagga aagcctttgg agtgatacca cagaaagtat ttatttttc tggaacattt    3900 agaaaaaact tggatcccta tgaacagtgg agtgatcaag aaatatggaa agttgcagat    3960
gaggttgggc tcagatctgt gatagaacag tttcctggga agcttgactt tgtccttgtg    4020
gatgggggct gtgtcctaag ccatggccac aagcagttga tgtgcttggc tagatctgtt    4080
ctcagtaagg cgaagatctt gctgcttgat gaacccagtg ctcatttgga tccagtaaca    4140
taccaaataa ttagaagaac tctaaaacaa gcatttgctg attgcacagt aattctctgt    4200
gaacacagga tagaagcaat gctggaatgc caacaatttt tggtcataga agagaacaaa    4260
gtgcggcagt acgattccat ccagaaactg ctgaacgaga ggagcctctt ccggcaagcc    4320
atcagcccct ccgacagggt gaagctcttt ccccaccgga actcaagcaa gtgcaagtct    4380
aagccccaga ttgctgctct gaaagaggag acagaagaag aggtgcaaga tacaaggctt    4440
tag                                                                  4443
```